(12) United States Patent
Miller et al.

(10) Patent No.: US 10,531,964 B2
(45) Date of Patent: Jan. 14, 2020

(54) PIVOTING WEDGE EXPANDING SPINAL IMPLANT AND METHOD OF IMPLANTING SAME

(71) Applicant: WARSAW ORTHOPEDIC, INC., Warsaw, IN (US)

(72) Inventors: Keith E. Miller, Germantown, TN (US); Anthony J. Melkent, Germantown, TN (US)

(73) Assignee: Wardaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 16/115,726

(22) Filed: Aug. 29, 2018

(65) Prior Publication Data

US 2018/0360615 A1 Dec. 20, 2018

Related U.S. Application Data

(62) Division of application No. 14/987,519, filed on Jan. 4, 2016, now Pat. No. 10,076,423.

(51) Int. Cl.
*A61F 2/44* (2006.01)
*A61F 2/30* (2006.01)

(52) U.S. Cl.
CPC ............ *A61F 2/447* (2013.01); *A61F 2/4455* (2013.01); *A61F 2002/30405* (2013.01); *A61F 2002/30466* (2013.01); *A61F 2002/30471* (2013.01); *A61F 2002/30507* (2013.01); *A61F 2002/30515* (2013.01); *A61F 2002/30538* (2013.01); *A61F 2002/30904* (2013.01); *A61F 2002/4475* (2013.01); *A61F 2220/0041* (2013.01)

(58) Field of Classification Search
CPC .. A61F 2/442; A61F 2002/443; A61F 2/4455; A61F 2/4465; A61F 2/447; A61F 2002/4475; A61F 2/446; A61F 2/4425; A61F 2/4611
See application file for complete search history.

(56) References Cited

U.S. PATENT DOCUMENTS

| | | |
|---|---|---|
| 7,850,733 B2 | 12/2010 | Byanham et al. |
| 7,875,078 B2 | 1/2011 | Wysocki et al. |
| 7,909,869 B2 | 3/2011 | Gordon et al. |
| 8,062,375 B2 | 11/2011 | Glerum et al. |
| 8,105,358 B2 | 1/2012 | Phan |
| 8,105,382 B2 | 1/2012 | Olmos et al. |
| 8,123,810 B2 | 2/2012 | Gordon et al. |
| 8,133,232 B2 | 3/2012 | Levy et al. |
| 8,187,332 B2 | 5/2012 | Mcluen |

(Continued)

FOREIGN PATENT DOCUMENTS

FR 2771282 5/1999

*Primary Examiner* — Julianna N Harvey

(57) ABSTRACT

A pivoting wedge expandable spinal implant. An upper portion and a lower portion are pivotally connected together. The implant, in a collapsed position, is inserted into a disc space. A driving screw engages and applies a force to a pushing portion, driving the pushing portion toward the implant's distal end. The pushing portion engages and drives a wedge toward the implant's distal end. The wedge pivots upward against an inner surface of the lower portion. The wedge continues to pivot along an inner surface of the upper portion, translating the force to the upper portion, pivoting and expanding the upper portion to an expanded position.

20 Claims, 12 Drawing Sheets

(56) References Cited

U.S. PATENT DOCUMENTS

| | | |
|---|---|---|
| 8,382,842 B2 | 2/2013 | Greenhalgh et al. |
| 8,394,145 B2 | 3/2013 | Weiman |
| 8,398,713 B2 | 3/2013 | Weiman |
| 8,403,990 B2 | 3/2013 | Dryer et al. |
| 8,435,298 B2 | 5/2013 | Weiman |
| 8,491,659 B2 | 7/2013 | Weiman |
| 8,518,120 B2 | 8/2013 | Glerum et al. |
| 8,523,944 B2 | 9/2013 | Jimenez et al. |
| 8,556,979 B2 | 10/2013 | Weiman et al. |
| 8,568,481 B2 | 10/2013 | Olmos et al. |
| 8,628,577 B1 | 1/2014 | Jimenez |
| 8,628,578 B2 | 1/2014 | Miller et al. |
| 8,632,595 B2 | 1/2014 | Weiman |
| 8,663,329 B2 | 3/2014 | Ernst |
| 8,679,183 B2 | 3/2014 | Glerum et al. |
| 8,685,098 B2 | 4/2014 | Glerum et al. |
| 8,709,086 B2 | 4/2014 | Glerum et al. |
| 8,778,025 B2 | 7/2014 | Ragab et al. |
| 8,795,366 B2 | 8/2014 | Varela |
| 8,888,853 B2 | 11/2014 | Glerum et al. |
| 8,888,854 B2 | 11/2014 | Glerum et al. |
| 8,894,711 B2 | 11/2014 | Varela |
| 8,894,712 B2 | 11/2014 | Varela |
| 8,926,704 B2 | 1/2015 | Glerum |
| 8,940,049 B1 | 1/2015 | Jimenez |
| 9,039,771 B2 | 5/2015 | Glerum et al. |
| 9,119,730 B2 | 9/2015 | Glerum et al. |
| 2008/0288071 A1 | 11/2008 | Biyani |
| 2010/0280622 A1* | 11/2010 | McKinley ............ A61F 2/4455 623/17.16 |
| 2011/0054621 A1 | 3/2011 | Lim |
| 2011/0172721 A1 | 7/2011 | Varela |
| 2011/0172774 A1 | 7/2011 | Varela |
| 2012/0035729 A1 | 2/2012 | Glerum et al. |
| 2012/0109319 A1 | 5/2012 | Perisic |
| 2012/0150304 A1 | 6/2012 | Glerum et al. |
| 2012/0150305 A1 | 6/2012 | Glerum et al. |
| 2012/0158146 A1 | 6/2012 | Glerum et al. |
| 2012/0158147 A1 | 6/2012 | Glerum et al. |
| 2012/0158148 A1 | 6/2012 | Glerum et al. |
| 2012/0185049 A1 | 7/2012 | Varela |
| 2012/0203347 A1* | 8/2012 | Glerum ................... A61F 2/447 623/17.16 |
| 2013/0144388 A1 | 6/2013 | Emery et al. |
| 2013/0158664 A1* | 6/2013 | Palmatier ................ A61F 2/447 623/17.16 |
| 2014/0058512 A1 | 2/2014 | Petersheim |
| 2014/0121774 A1 | 5/2014 | Glerum et al. |
| 2014/0236296 A1* | 8/2014 | Wagner ................... A61F 2/447 623/17.15 |
| 2014/0277500 A1 | 9/2014 | Logan |
| 2014/0324171 A1 | 10/2014 | Glerum et al. |
| 2015/0012097 A1* | 1/2015 | Ibarra .................... A61F 2/447 623/17.15 |
| 2015/0272743 A1 | 10/2015 | Jimenez |
| 2015/0374508 A1* | 12/2015 | Sandul ................... A61F 2/447 623/17.16 |
| 2016/0022438 A1* | 1/2016 | Lamborne ............ A61F 2/4455 623/17.16 |
| 2017/0112630 A1* | 4/2017 | Kuyler .................... A61F 2/447 |

\* cited by examiner

# PIVOTING WEDGE EXPANDING SPINAL IMPLANT AND METHOD OF IMPLANTING SAME This application is a divisional of U.S. application Ser. No. 14/987,519 filed Jan. 4, 2016; all of which is incorporated herein by reference.

BACKGROUND OF THE INVENTION

Field of the Invention

The present invention relates to a spinal implant. More particularly, the invention relates to an expandable spinal implant having a pivoting wedge, configured to expand within a patient's disc space between two adjacent vertebral bodies, from a collapsed position to an expanded position.

Description of the Related Art

Expandable spinal implants are known in the art. Such expandable implants can be configured to have lordotic, tapered configurations to assist in the restoration or enhancement of spinal lordosis. The expandability of such implants allows placement of the implant, while in a collapsed position, through a relatively small opening in a patient's body, into a corresponding surgically-enhanced disc space between two adjacent vertebral bodies. Thereafter, expansion of the implant within the disc space increases the height between the two adjacent vertebral bodies, assisting in the restoration or enhancement of spinal lordosis.

The related art expandable implants typically have two components, pivotally held together by a pivot pin. During expansion of the implant to the expanded position, the pin, in some cases, may be incapable of withstanding all of the forces generated between the two components, resulting in damage to, and inoperabilty of, the implant.

SUMMARY OF THE INVENTION

It is an object of the present invention to provide an expandable spinal implant which obviates one or more of the shortcomings of the related art.

It is another object of the present invention to provide a pivoting wedge expandable spinal implant for insertion into a patient's disc space between an upper vertebral body and a lower vertebral body. The implant has a proximal end and a distal end defining a mid-longitudinal axis. The implant is expandable between a collapsed position and an expanded position. The implant includes an upper portion. The upper portion has a proximal end and a distal end. The upper portion also has an inner surface and an outer surface. The outer surface is configured to engage a vertebral endplate of the upper vertebral body. The inner surface has an upper ramp surface.

The implant further includes a lower portion. The lower portion is pivotally engaged with the upper portion, and has a proximal end and a distal end. The proximal end includes a threaded proximal end opening. The lower portion also has an inner surface and an outer surface. The outer surface is configured to engage a vertebral endplate of the lower vertebral body. The inner surface includes a lower ramp surface. The lower ramp surface and the upper ramp surface define an internal pocket therebetween.

A force application device is configured to be inserted into the proximal end threaded opening. The force application device includes a distal end.

A pushing portion is defined in the proximal end of the implant. The pushing portion has a proximal end and a distal end. The proximal end of the pushing portion is configured to come into contact with the distal end of the force application device.

A wedge is defined in the distal end of the implant. The wedge has a proximal end and a distal end. The proximal end of the wedge is configured to be in contact with the distal end of the pushing portion. The distal end of the wedge is configured to be positioned, when the implant is in the collapsed position, within the internal pocket defined by the upper ramp surface and the lower ramp surface. The distal end of the wedge is further configured, when force is applied by the force application device to the pushing portion, forcing the pushing portion to move in the direction of the distal end of the implant, to be moved, by the pushing portion, up along the lower ramp surface and into contact with the upper ramp surface, translating the motion to the upper ramp surface, thereby and moving the upper ramp portion away from the lower ramp portion. The distal end of the wedge further moves up along the upper ramp surface, further expanding the implant until it reaches the expanded position.

It is a further object of the present invention to provide a method of inserting the expandable spinal implant as described above into a patient's disc space between an upper vertebral body and a lower vertebral body.

The method includes surgically preparing a disc space between a lower vertebral body and an upper vertebral body, inserting the implant described above, in the collapsed position, into the disc space, with the force application device applying a force to the pushing portion, thereby pushing the pushing portion toward the distal end of the implant, pushing the wedge toward the distal end of the implant, up the lower ramp surface and into contact with at least a portion of the upper ramp surface, translating the force to the upper ramp surface, moving the upper ramp portion away from the lower ramp portion, pushing the distal end of the wedge up the upper ramp surface, and expanding the implant to the expanded position.

These and other objects of the present invention will be apparent from review of the following specification and the accompanying drawings.

DETAILED DESCRIPTION OF THE PREFERRED EMBODIMENT

Figure 1:
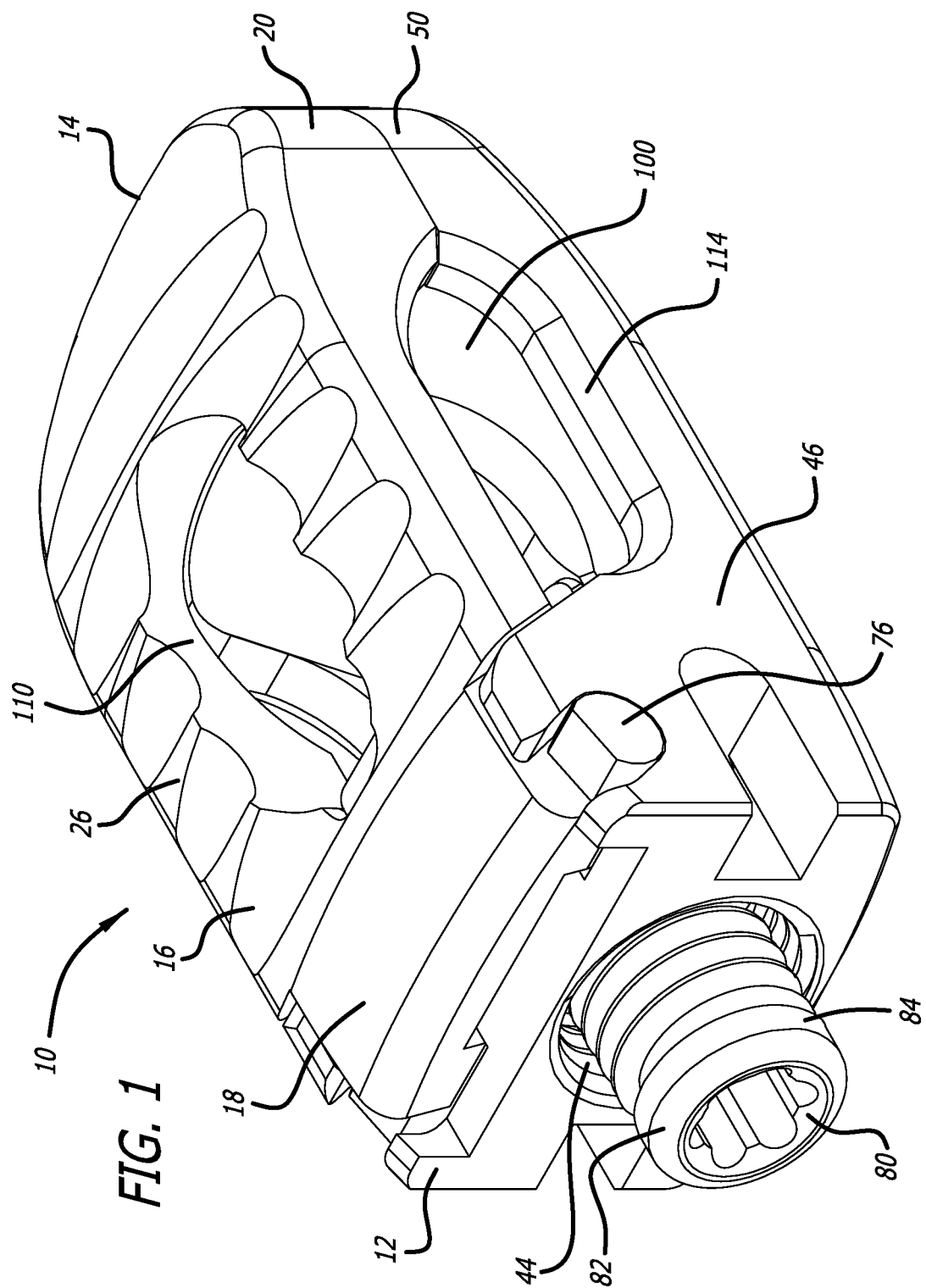
FIG. 1 is a lower perspective view of a pivoting wedge expandable spinal implant in accordance with the invention.

In accordance with the invention, and as depicted in FIGS. 1-15, a pivoting wedge expandable spinal implant 10 is provided, configured to be inserted in a surgically-enhanced disc space between an upper vertebral body and a lower vertebral body (not shown). The implant includes a proximal end 12 and a distal end 14, defining a mid-longitudinal axis L-L therebetween.

In accordance with the invention, the implant includes an upper portion 16. The upper portion 16 includes a proximal end 18, a distal end 20, an inner surface 22, and an outer surface 24.

Figure 2:
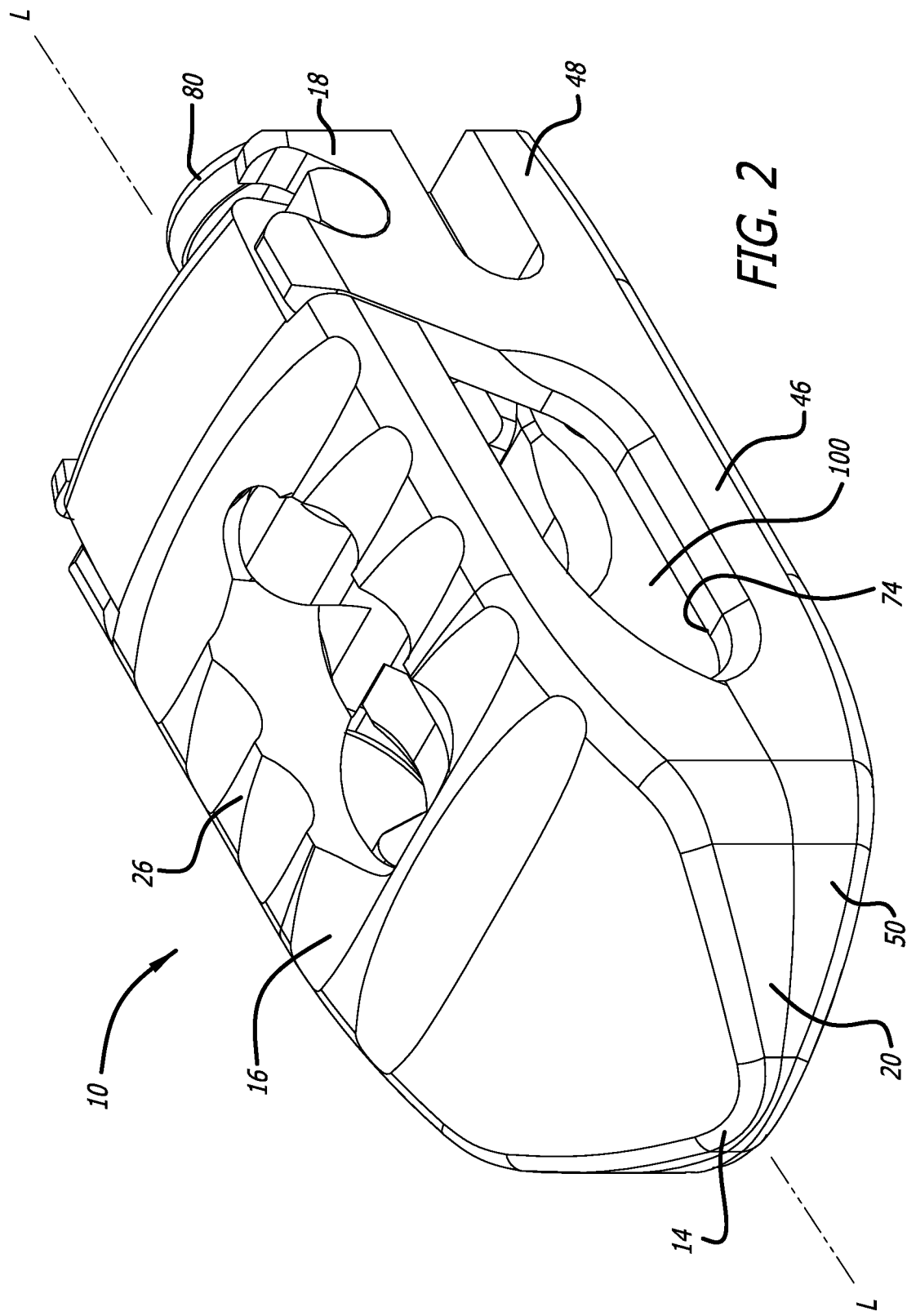
FIG. 2 is an upper perspective view of a pivoting wedge expandable spinal implant in accordance with the invention.

In accordance with the invention, and as depicted in FIG. 2, the distal end 14 is preferably tapered, for simplicity of access to the disc space.

The outer surface 24 includes one or more raised ridges 26, for engaging a vertebral endplate of the upper vertebral body.

Figures 3, 3A:
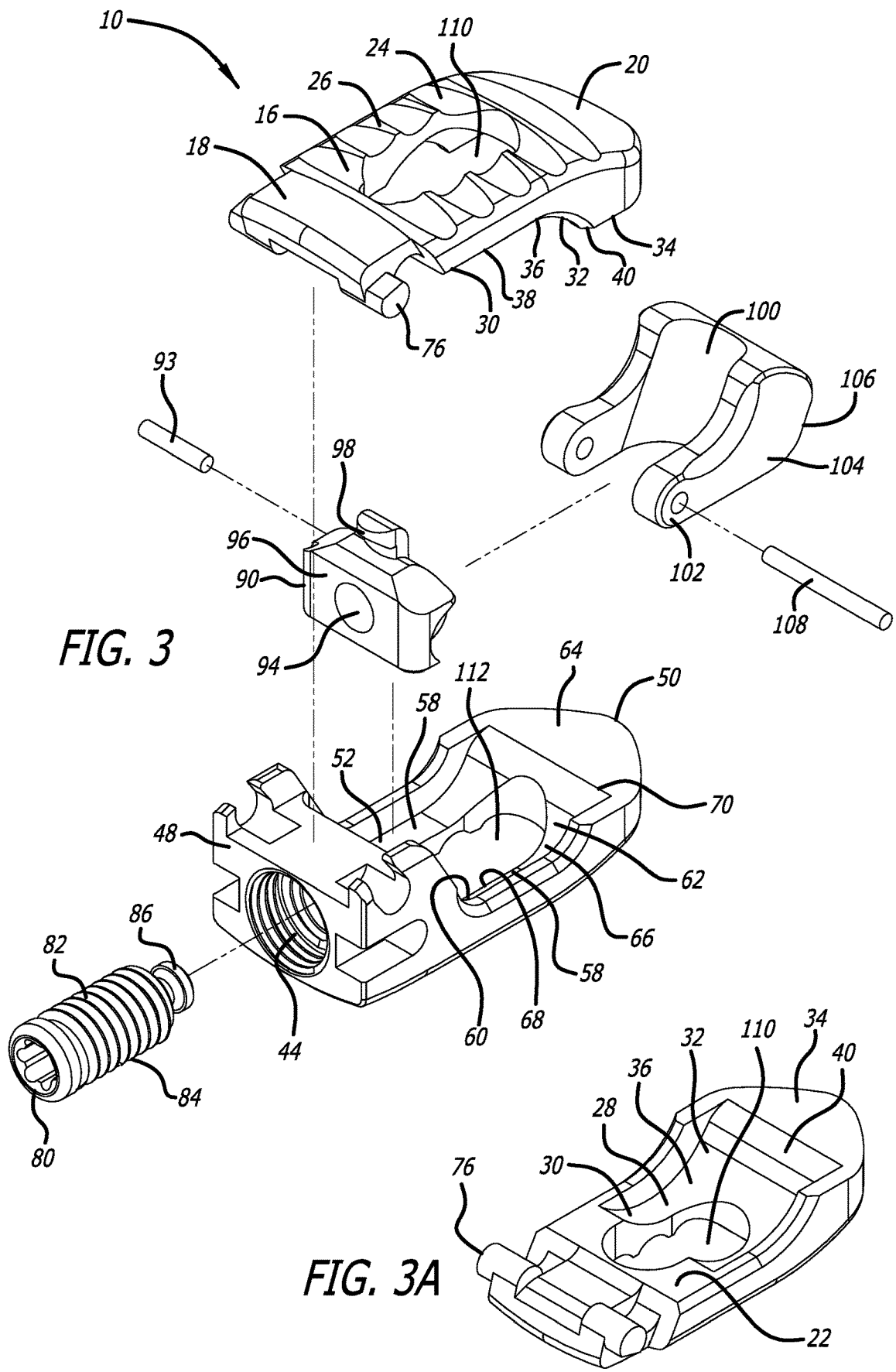
FIG. 3 is an exploded parts view of a pivoting wedge expandable spinal implant in accordance with the invention.
FIG. 3A is a perspective view of an upper portion of the pivoting wedge expandable spinal implant in accordance with the invention, flipped over to depict an interior configuration of the upper portion, including an upper ramp portion.
Figure 15:
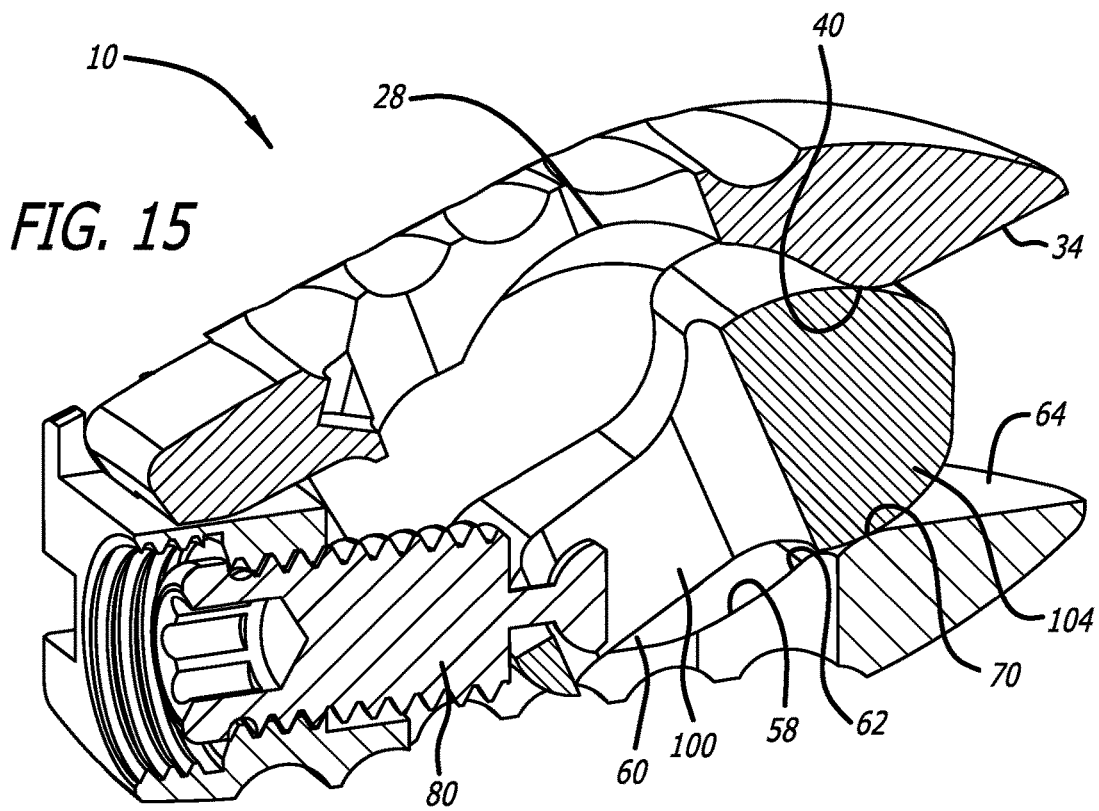
FIG. 15 is a lower perspective cross-sectional view of a pivoting wedge expandable spinal implant in accordance with the invention, without a pushing portion, and with a distal end of the force application device configured to contact a proximal end of the wedge, expanded to an 80% expanded position.
Figure 16:
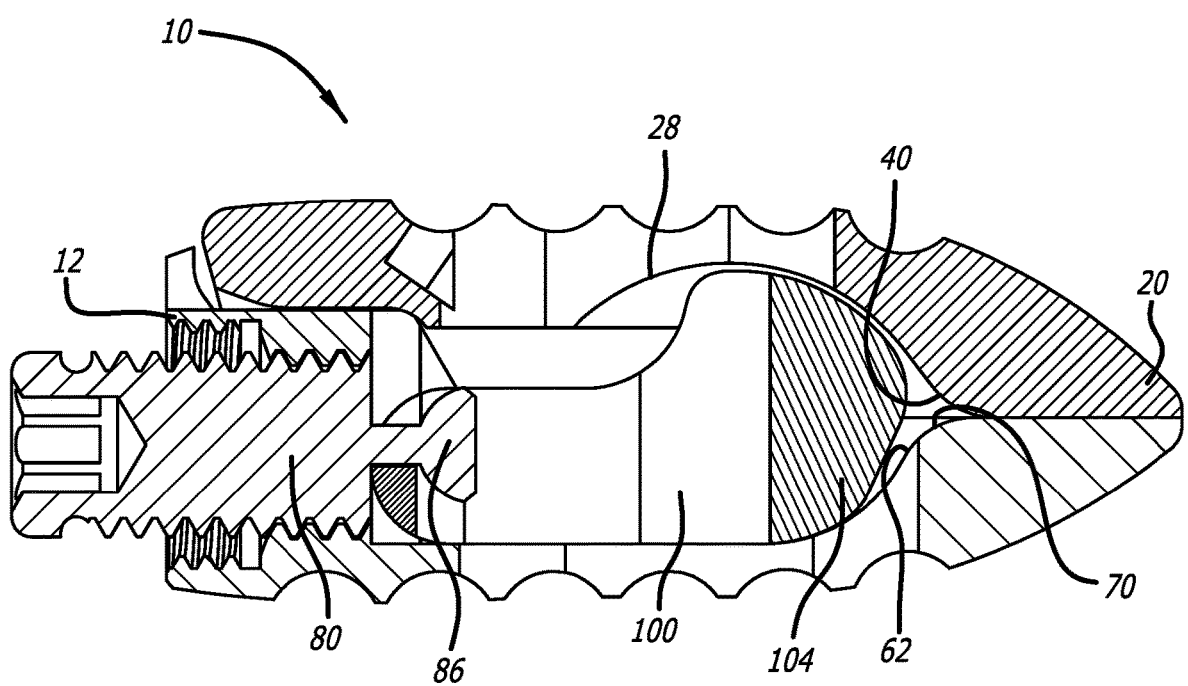
FIG. 16 is a side cross-sectional view of the pivotal wedge expandable spinal implant depicted in FIG. 15, in the collapsed position.

In accordance with the invention, and as depicted in FIGS. 3, 3A, and 15, the inner surface 22 defines an upper ramp surface 28. The upper ramp surface 28 extends from a first position 30 intermediate the proximal end 18 and the distal end 20, to a second position 32 proximate the distal end 14 of the implant 10. A first planar surface 34 extends from the second position 32 to the distal end 14 of the implant 10. The upper ramp surface 28 includes an arcuate portion 36 proximate the second position 32. The arcuate portion 36 intersects with the first planar surface 34 at a first transition point 40. The invention is not limited to the configuration of the upper ramp surface 28 described above. Additional configurations for the upper ramp surface 28 are conceivable and within the scope of the invention, including, but not limited to, a substantially planar surface parallel to the longitudinal axis.

In accordance with a preferred embodiment of the invention, the implant includes a lower portion 46. The lower portion 46 includes a proximal end 48, a distal end 50, an inner surface 52, and an outer surface 54. The outer surface 54 includes one or more raised ridges 56, for engaging a vertebral endplate of the lower vertebral body. The inner surface 52 defines a lower ramp surface 58.

In accordance with the invention, and as depicted in FIGS. 3 and 15, the lower ramp surface 58 extends from a first position 60 intermediate the proximal end 48 and the distal end 50 to a second position 62 proximate the distal end 14 of the implant 10. A first planar surface 64 extends from the second position 62 to the distal end 14 of the implant 10. The lower ramp surface 58 includes an arcuate portion 66 proximate the second position 62. The arcuate portion 66 intersects with the first planar surface 64 at a second transition point 70. The lower portion 46 further includes, at the proximal end 48, a threaded proximal aperture 44. The invention is not limited to the configuration of the lower ramp surface 58 described above, and depicted in FIGS. 3, 3A and 15. Additional configurations for the lower ramp surface 58 are conceivable and within the scope of the invention, including, but not limited to, a substantially planar surface proximate the first position 60, which ramps upward transverse to the mid-longitudinal axis, defining the ramp surface 58, to the arcuate position 66 proximate the second position 62. The lower ramp surface 58 combines with the upper ramp surface 28 to define an internal pocket 74, internal to the implant 10.

Figure 4:
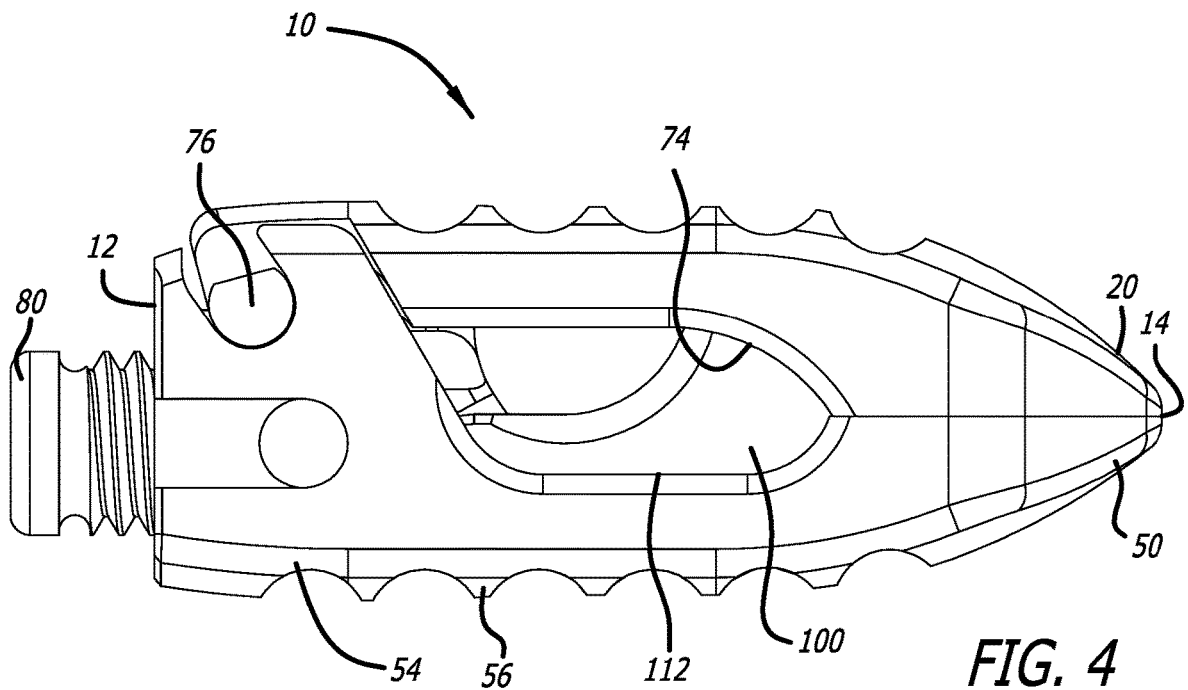
FIG. 4 is a side view of a pivoting wedge expandable spinal implant in accordance with the invention in the collapsed position.

In accordance with a preferred embodiment of the invention, and as depicted in FIG. 4, the upper portion 16 is pivotally connected to the lower portion 46 via a hinge 76 defined at the proximal end 12 of the implant 10.

Figure 5:
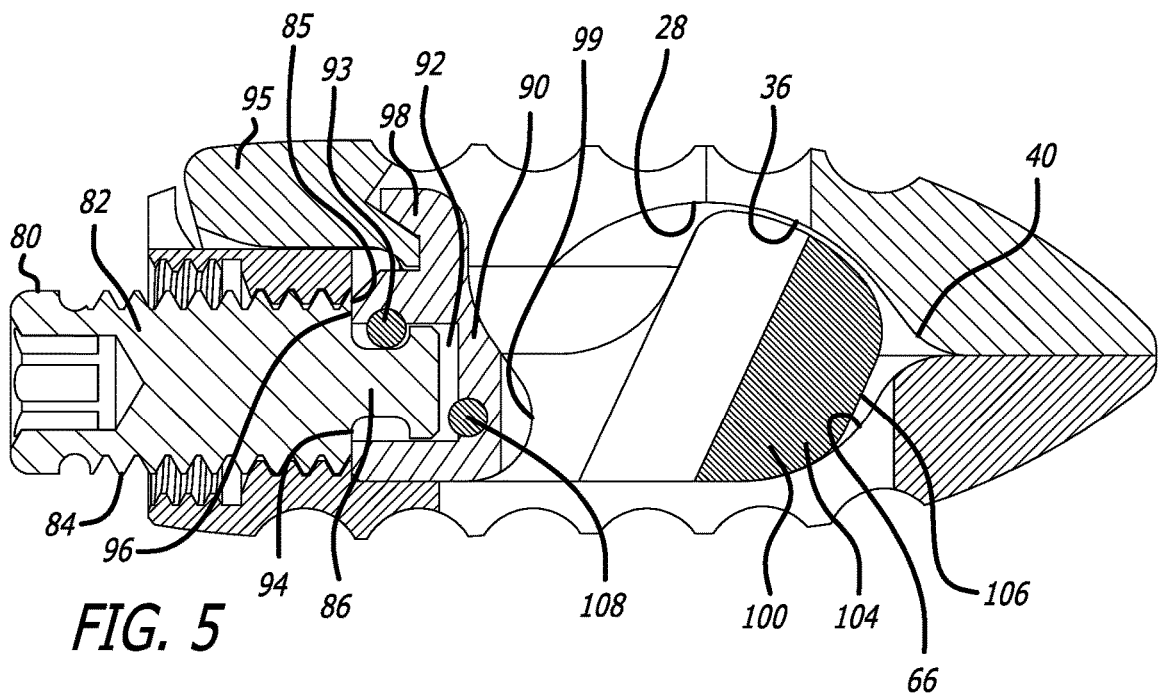
FIG. 5 is a side cross-sectional view of a pivoting wedge expandable spinal implant in accordance with the invention in the collapsed position.

In accordance with a preferred embodiment of the invention, a force application device 80 is provided. As depicted in FIGS. 1-8, force application device 80 is a screw, having a shaft 82. Shaft 82 includes threads 84, a T-shaped distal end 86, and a distal surface 85 that is perpendicular to the mid-longitudinal axis. In the embodiment of FIG. 5, distal surface 85 includes a distal thread. The invention, however, is not limited to use of a screw as the force application device 80, nor is the invention limited to use of a distal thread as the distal surface 85.

In accordance with one embodiment of the invention, a pushing portion 90 is defined in the proximal end 12 of the implant 10. As depicted in FIGS. 5-9, pushing portion 90 includes a proximal end pocket 92. The proximal end pocket 92 includes an opening 94 defined in the proximal end of the proximal end pocket 92. A vertical wall 96 is defined on the pushing portion 90 adjacent the proximal end pocket 92. The pushing portion 90 further includes a hook-shaped projection 98. As depicted in FIG. 5, when the implant 10 is in the collapsed position, the hook-shaped projection 98 engages a locking portion 95 on the upper portion 16 to hold the implant 10 in the collapsed position. As depicted in FIG. 8, however, when the implant 10 is being moved to the expanded position, the force application device is moved through the proximal aperture 44. The hook-shaped projection 98 is pushed away from the locking portion 95 to allow the implant 10 to expand. The T-shaped distal end 86 of the force application device 80 is configured to insert through the opening 94, and move into the proximal end pocket 92 of the pushing portion 90, where it is held in place via a pin 93. The distal surface 85 comes into contact with the vertical wall 96 adjacent the proximal end pocket 92, moving the pushing portion 90 towards the distal end 14 of the implant 10. The motion is then translated by the pushing portion 90, moving the pushing portion 90 toward the distal end 14 of the implant 10.

In accordance with another preferred embodiment of the invention, as depicted in FIG. 8, the pushing portion 90 also includes a distal end pocket 99.

In accordance with a preferred embodiment of the invention, a wedge 100 is provided proximate the distal end 14 of the implant 10. The wedge 100 includes a proximal end 102 and an arcuate distal end 104. The proximal end 102 of the wedge 100 is connected to the pushing portion 90. In one embodiment of the invention, as depicted in FIG. 5, the proximal end 102 of the wedge 100 is attached to the pushing portion 90 with a pin 108. As depicted in FIG. 8, the proximal end 102 of the wedge 100 also can be configured to be engaged to the pushing portion 90 by contact with the distal end pocket 99.

In accordance with another embodiment of the invention, the outer surface 24 of the upper portion 16, and the outer surface 54 of the lower portion 46 are each configured with upper and lower apertures 110, 112, respectively. The upper and lower apertures 110 and 112 provide openings to the internal pocket 74. In addition, the sides of the implant 10 in this embodiment define side apertures 114. In this embodiment of the invention, after the implant 10 is in place in the disc space, bone-growth material packed into the internal pocket 74 of the implant 10 can grow through the respective openings 110, 112, and 114. Suitable bone graft material is well-known in the art. In particular, the side apertures 114 allow the implant 10 to be packed with bone graft material after the implant 10 has been inserted into the disc space.

Figure 9:
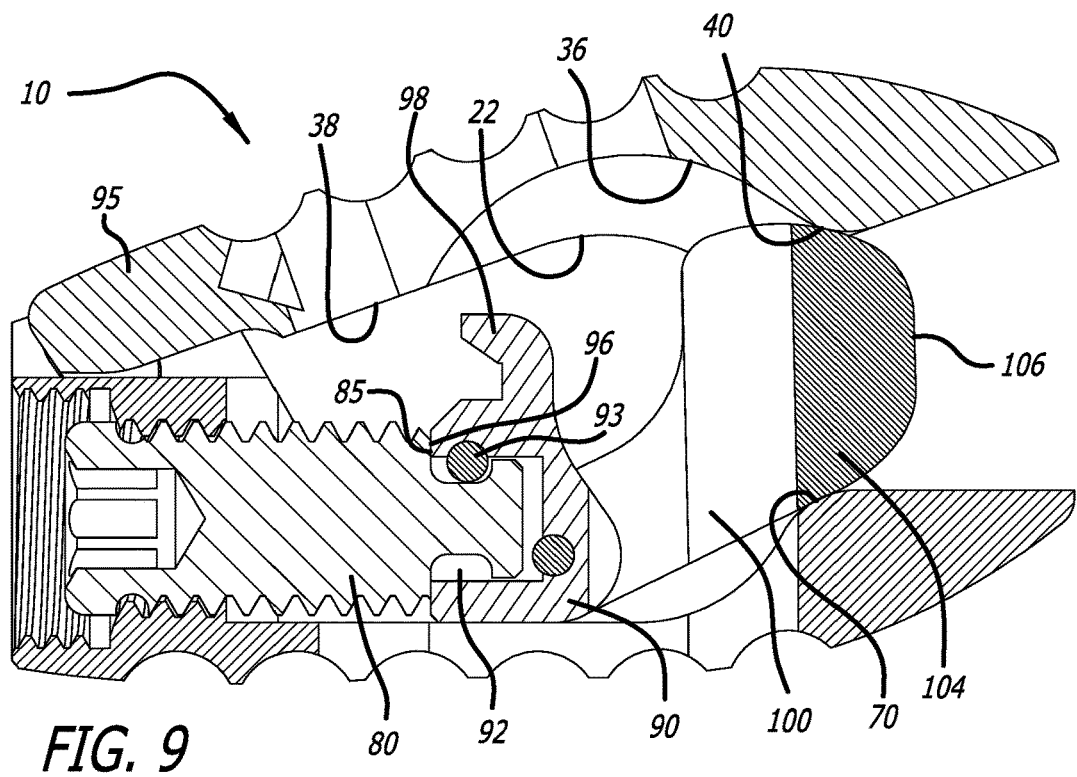
FIG. 9 is a side cross-sectional view a pivoting wedge expandable spinal implant in accordance with the invention expanded to the 100% expanded position.
Figure 11:
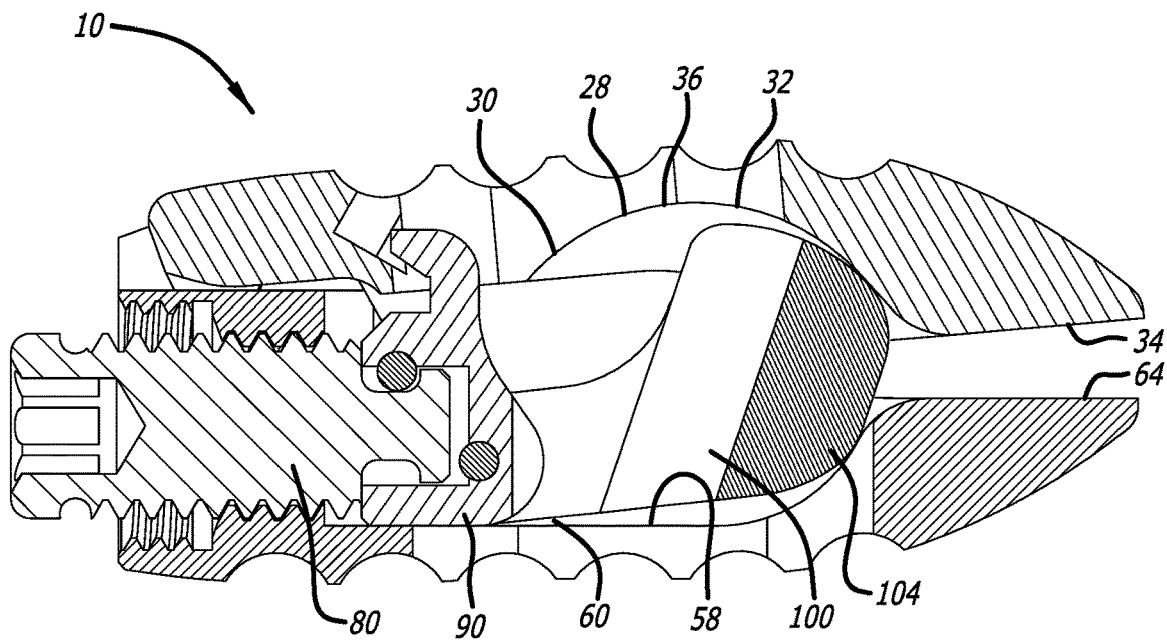
FIG. 11 is a side cross-sectional view of a pivoting wedge expandable spinal implant in accordance with the invention, expanded to the 20% expanded position.
Figure 12:
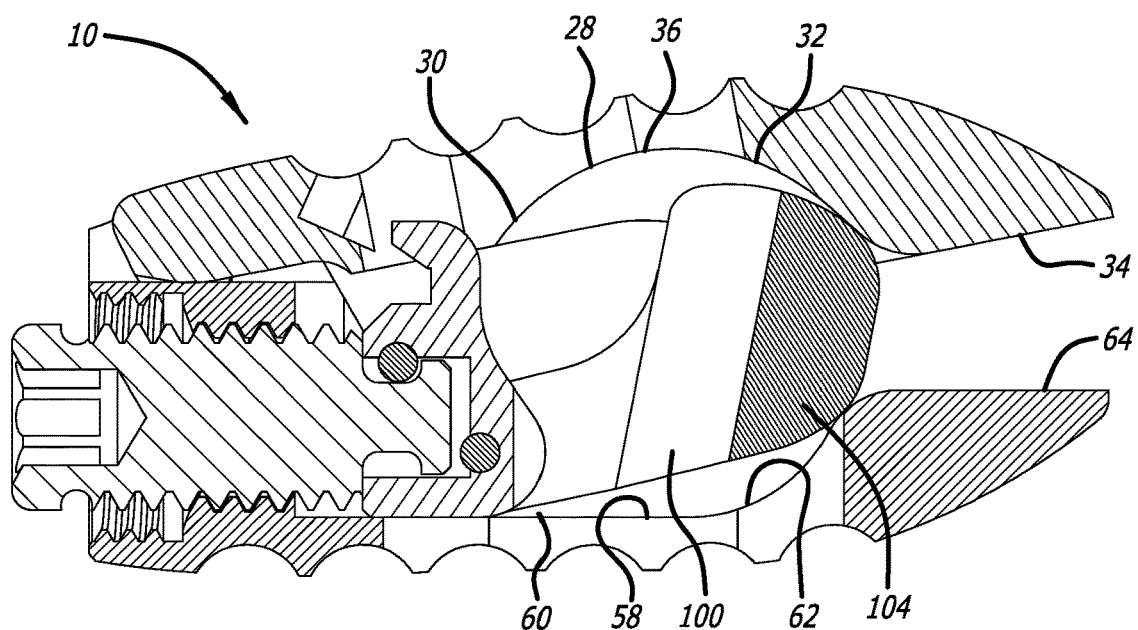
FIG. 12 is a side cross-sectional view of a pivoting wedge expandable spinal implant in accordance with the invention, expanded to the 40% expanded position.
Figure 13:
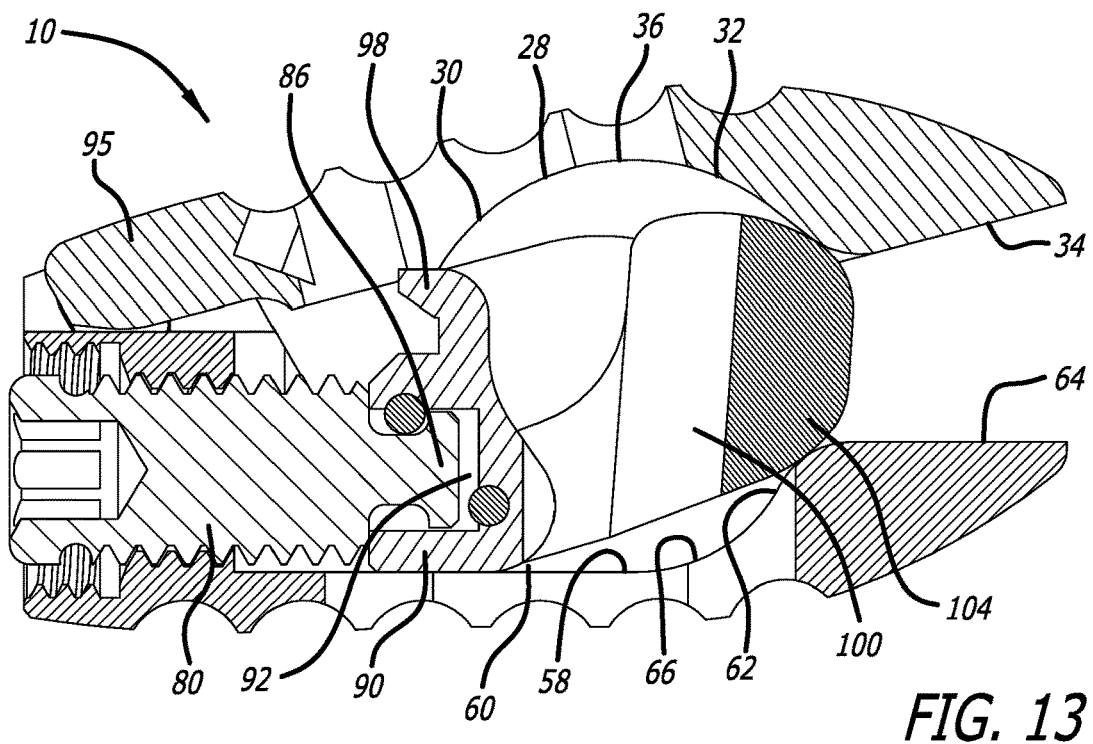
FIG. 13 is a side cross-sectional view of a pivoting wedge expandable spinal implant in accordance with the invention, expanded to the 60% expanded position.
Figure 14:
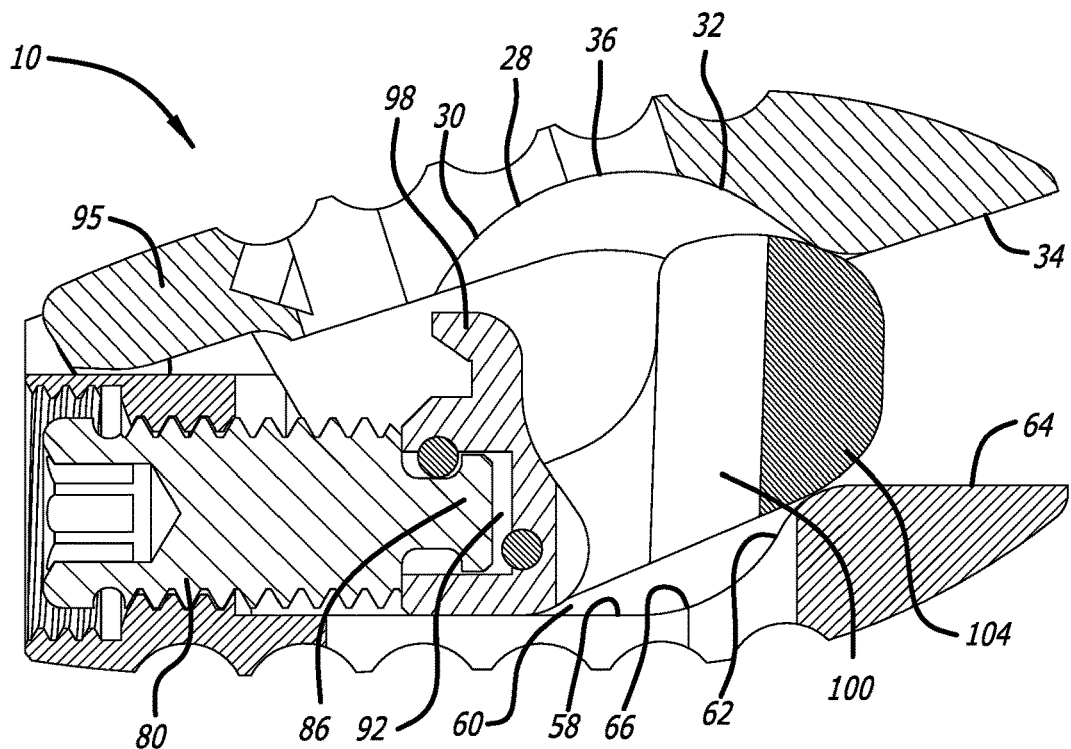
FIG. 14 is a side cross-sectional view of a pivoting wedge expandable spinal implant in accordance with the invention, expanded to the 80% expanded position.

In accordance with a preferred embodiment of the invention, the implant 10 is configured, such that, commencing in the collapsed position, as depicted in FIG. 5, upon translation of the motion from the force application device 80 to the pushing portion 90, subsequent distal motion of the pushing portion 90 is translated to the proximal end 102 of the wedge 100. As depicted in FIG. 11, the arcuate distal end 104 of the wedge 100 moves out of the internal pocket 74, and moves up along the arcuate portion 66 of the lower ramp surface 58 towards the second transition point 70. At this point, as depicted in FIG. 11, the implant 10 is approximately 20% open. As depicted in FIGS. 11 and 12, the wedge 100 moves past the first transition point 40 of the upper ramp surface 28. As depicted in FIG. 12, the implant is approximately 40% open. Subsequently, as depicted in FIGS. 13 and 14, the external radius 106 of the arcuate distal end 104, moves along the internal upper ramp surface 28. In this manner, the force applied to the pushing portion 90 by the force application device 80 is translated into movement of the upper portion 16, thereby pivoting the upper portion 16 on hinge 76, and moving the upper portion 16 away from, the lower portion 46. As depicted in FIG. 13, the implant 10 is approximately 60% open. As depicted in FIG. 14, the implant 10 is approximately 80% open. Movement of the upper portion 16 will continue until the implant 10 achieves the expanded position (i.e., approximately 100% expanded, as depicted in FIG. 9).

Figure 10:
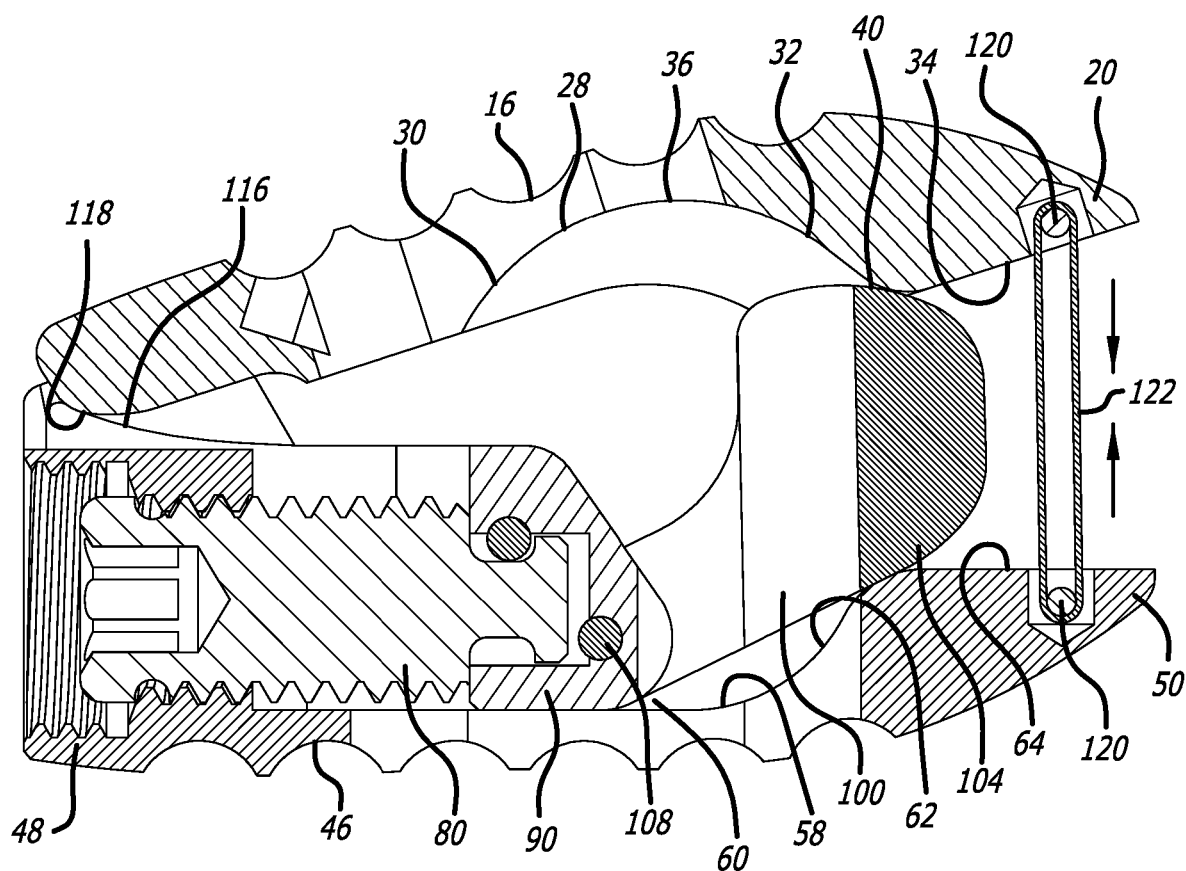
FIG. 10 is a side cross-sectional view of a pivoting wedge expandable spinal implant in accordance with another embodiment of the invention.

In accordance with another embodiment of the invention, as depicted in FIG. 10, the implant 10 may include an arcuate posterior ramp portion 116 defined on the pushing portion 90. As depicted in FIG. 10, the proximal end 18 of the upper portion 16 includes an arcuate portion 118. The arcuate posterior ramp portion 116 has a radius which is larger than a radius of the arcuate posterior ramp portion 118. Alternatively, the posterior ramp portions may have straight inclines, or multiple curves. Interaction between these two arcuate components further moves the upper portion 16 of the implant 10 away from the lower portion 46 of the implant 10.

In accordance with another embodiment of the invention, as depicted in FIG. 10, the distal end 14 of the implant 10 may include distal end projecting pins 120 projecting from the upper portion 16 and the lower portion 46. An elastic member 122 may be wrapped around the distal end projecting pins 120. Upon translation of the force application device from the distal end of the implant, the elastic member 122 assists pulling the upper portion 16 and the lower portion 46 back together in the collapsed position.

In accordance with a preferred embodiment of the invention, a disc space of a patient between an upper vertebral body and a lower vertebral body is surgically prepared. An implant 10, having the configuration of the invention as described above, is inserted into the disc space, either via a posterior approach, or via a lateral approach. The implant 10 is inserted into the disc space in the collapsed position. The ridges 26 on the outer surface 24 of the upper portion 16 engage a vertebral endplate of the upper vertebral body. Likewise, the ridges 56 on the outer surface 54 of the lower portion 46 engage a vertebral endplate of the lower vertebral body. As depicted in FIG. 5, the hook-shaped projection 98 on the pushing portion 90 is engaged with the locking portion 95 of the upper portion 16, assisting in holding the upper portion 16 in place over the lower portion 46, assisting in keeping the implant 10 in the collapsed position.

In accordance with a preferred embodiment of the invention, the force application device 80, preferably in the form of a threaded screw, is moved in the threaded proximal aperture 44 toward the distal end 20 of the implant 10. The T-shaped distal end 86 is held in place in the proximal end pocket 92 by the pin 93. The distal surface 85 contacts the vertical wall 96 adjacent the proximal end pocket 92, translating motion of the force application device 80 to the pushing portion 90. The pushing portion 90 moves toward the distal end 14 of the implant 10. This motion causes the hook-shaped projection 98 to be disengaged from the locking portion 95 on the upper portion 16.

Figure 6:
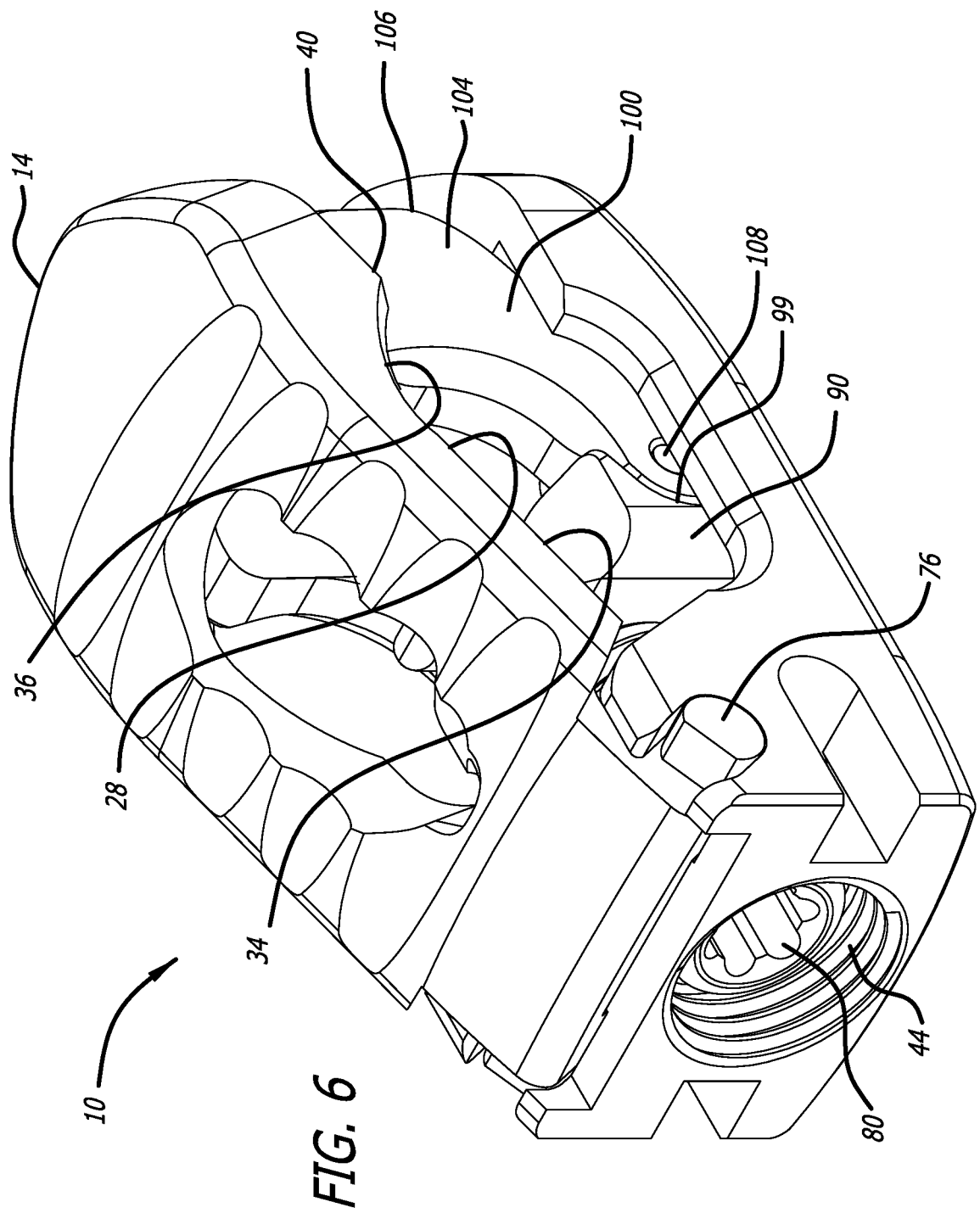
FIG. 6 is a lower perspective view of a pivoting wedge expandable spinal implant in accordance with the invention in the process of expanding to the expanded position.
Figure 7:
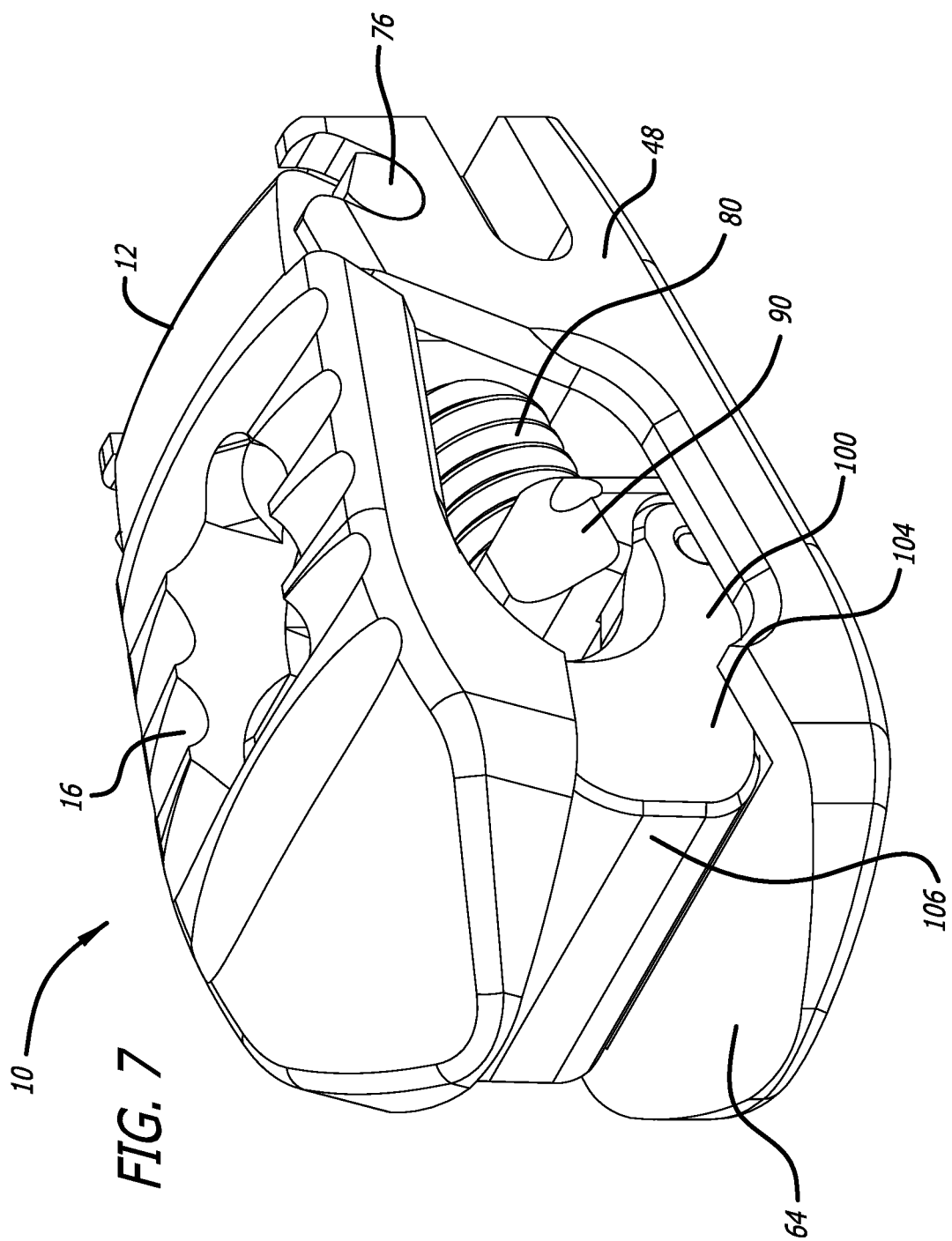
FIG. 7 is an upper perspective view of a pivoting wedge expandable spinal implant in accordance with the invention in the process of expanding to the expanded position.
Figure 8:
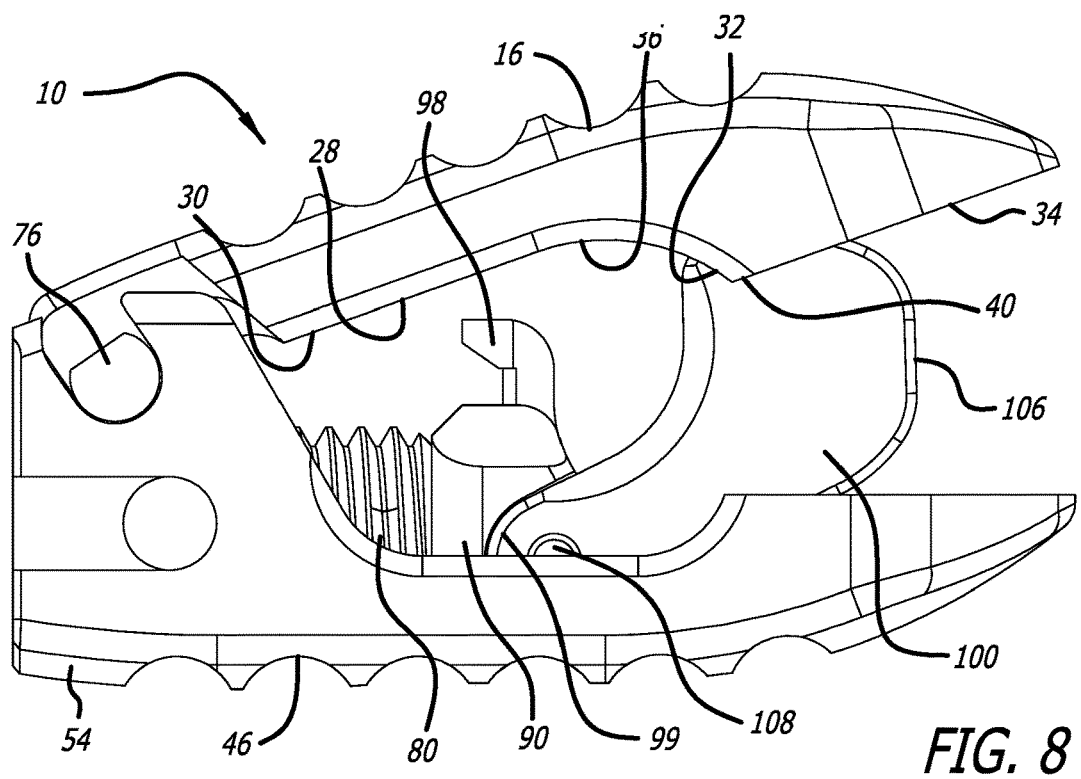
FIG. 8 is a side view of a pivoting wedge expandable spinal implant in accordance with the invention in the process of expanding to the expanded position.

In accordance with a preferred embodiment of the invention, and as depicted in FIGS. 5-7, the motion of the pushing portion 90 is subsequently translated to the proximal end 12 of the wedge 100. The wedge 100 moves toward the distal end 14 of the implant 10, while the pin 108 may or may not remain unloaded. The arcuate distal end 104 of the wedge 100 is pushed out of the internal pocket 74, and up the lower ramp surface 58, past the second transition point 70, and into contact with the first transition point 40 on the upper portion 16. Motion translated to the upper portion 16, causes the upper portion 16 to rotate upward on hinge 76, away from lower portion 46.

In accordance with a preferred embodiment of the invention, as the upper portion 16 commences to move the arcuate distal end 104 of the wedge 100 moves along the upper ramp surface 28, moving the upper portion away from the lower portion. The arcuate distal end 104 of the wedge 100 continues to move up the upper ramp surface 28 until the implant 10 has reached the expanded position.

In accordance with the invention, in the process of being expanded from the collapsed position to the expanded position, the wedge 100 both pivots and engages two ramps, while the pin 108 may or may not remain unloaded. The internal pocket 74 between the upper ramp surface 28 and the lower ramp surface 58 carries the majority of all of the force between the pushing portion 90 and the components of the wedge 100. The resulting degree of expansion in the expanded position of the implant 10 is significantly increased when compared to a non-pivoting wedge. The increased degree of expansion of the implant 10 in the expended position results in an increased angle between the lower portion 46 and the upper portion 16. This increased angle results in increased lordosis between the upper and lower vertebral bodies.

Figure 17:
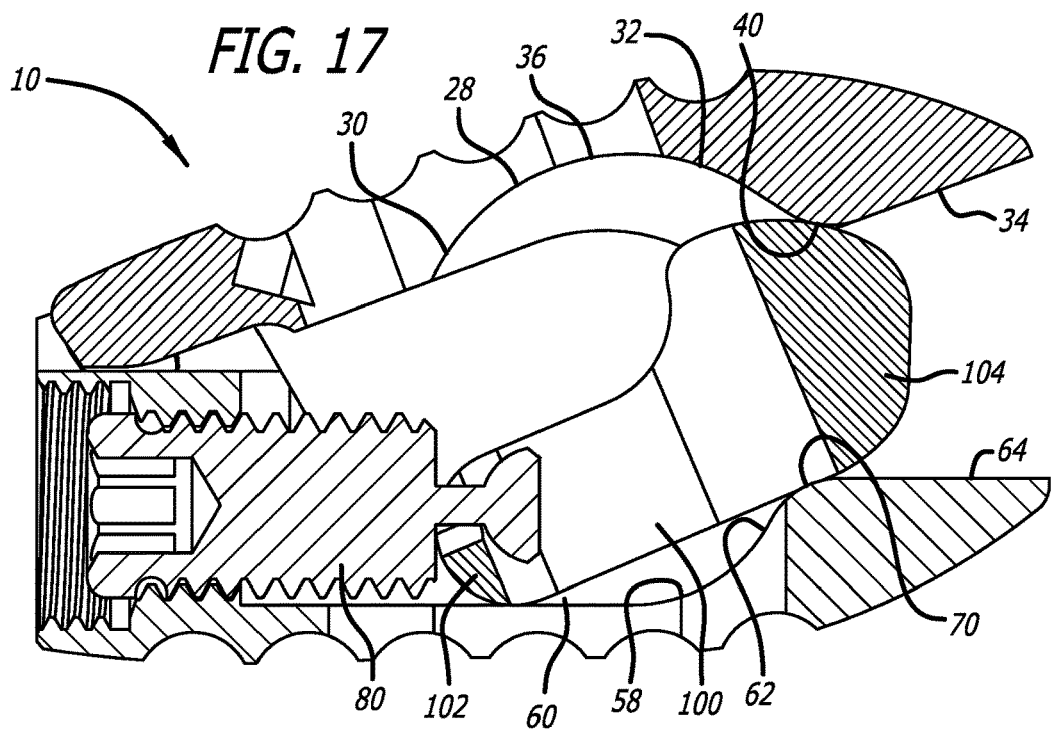
FIG. 17 is a lower perspective cross-sectional view of the pivoting wedge expandable spinal implant depicted in FIG. 15, expanded to a 40% expanded position.
Figure 18:
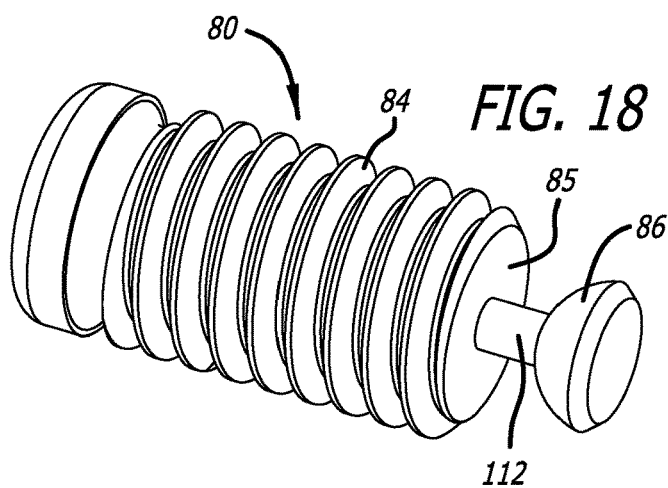
FIG. 18 is an upper perspective view of a threaded force application device, used in the pivotal wedge expandable spinal implant depicted in FIG. 15.
Figure 19:
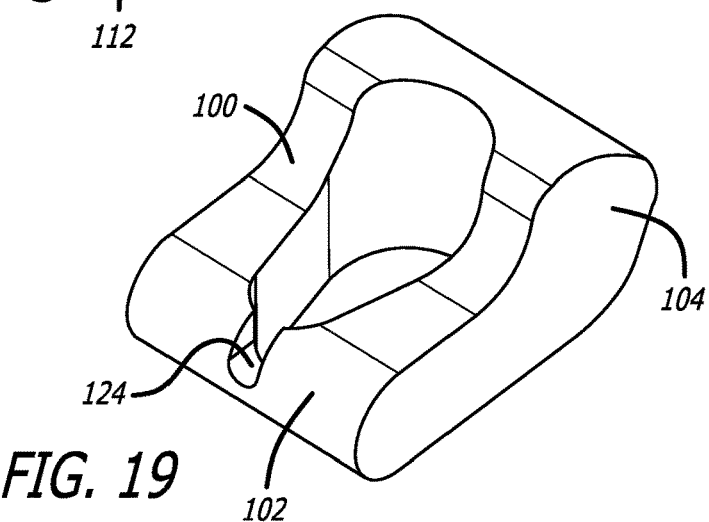
FIG. 19 is an upper perspective view of a wedge, used in the pivotal wedge expandable spinal implant depicted in FIG. 15.

In accordance with another preferred embodiment of the invention, as depicted in FIGS. 17-19, the implant 10 does not include a pushing portion 90. In this embodiment, a stem 112 of the T-shaped distal end 86 of the force application device 80 fits into a notch 124 defined in the proximal end 102 of the wedge 100. With this configuration the force application device 80 is positioned to translate motion directly to the proximal end 102 of the wedge 100. Rotation of the threaded force application device 80 in the threaded proximal aperture 44 moves the force application device 80 toward the distal end 14 of the implant 10. Contact between the distal surface 85 of the force application device 80 with the distal end 102 of the wedge 100 translates the motion of the force application device 80 directly to the wedge 100, thereby moving the wedge 100 toward the distal end 14 of the implant 10. The wedge 100 is moved along the lower ramp surface 58 into contact with the upper ramp surface 28. The wedge 100 moves along the upper ramp surface 28, rotating the upper ramp surface 28, on the hinge 76, away from the lower ramp surface 58, until the implant 10 reaches the expanded position.

Other embodiments of the invention will be apparent to those skilled in the art from consideration of the specification and practice of the invention disclosed herein. For example, and not by way of limitation, a modular upper portion 16 can be removed, e.g., by disconnecting the modular upper portion 16 from the lower portion 46 at the hinge 76, and replacing the removed modular upper portion with another modular upper portion 16, which may have different dimensions. In addition, all of the components described above as being associated with the upper portion, and all of the components described above as being associated with the lower portion can be switched, i.e., the upper and lower portions can be entirely reversed in orientation, and the resultant implant would still fall within the spirit and scope of the present invention. The specification and examples are to be considered as exemplary only, with a true scope and spirit of the invention being indicated by the following claims.

We claim:

1. A method of inserting an expandable spinal implant into a disc space of a patient between an upper vertebral body and a lower vertebral body, the method comprising:
   providing an expandable spinal implant, the implant having a proximal end, an opposite distal end, an upper portion, a lower portion, a moveable portion, and a force application device, the upper portion and the lower portion being expandable between a collapsed position and an expanded position, the moveable portion being positioned between the upper portion and the lower portion, and the force application device being configured to move the moveable portion toward or away from the distal end of the implant;
   surgically preparing the disc space;
   inserting the implant, with the upper portion and the lower portion in the collapsed position, into the disc space;
   applying a force with the force application device to a wedge portion of the moveable portion;
   moving the wedge portion toward the distal end of the implant along a lower surface formed on the lower portion;
   pivoting the wedge portion along a ramp portion of the lower surface of the lower portion toward at least a portion of an upper surface formed on the upper portion;
   contacting the wedge portion to the upper portion and moving the upper portion away from the lower portion; and
   expanding the implant to the expanded position.

2. The method of claim 1, wherein at least one of the upper and lower surfaces includes at least one opening defined therein.

3. The method of claim 2, further comprising placing a bone growing agent through the at least one opening defined in the at least one of the upper surface and the lower surface.

4. The method of claim 1, wherein moving the upper portion away from the lower portion increases lordosis between the upper vertebral body and the lower vertebral body.

5. The method of claim 1, wherein the upper portion and the lower portion are pivotally engaged with one another, the upper portion includes an inner surface of which the upper surface is a part, the inner surface of the upper portion extends from a position intermediate the distal end and the proximal end to a second position proximate the distal end, the lower portion includes an inner surface of which the lower surface is a part, the inner surface of the lower portion extends from a position intermediate the distal end and the proximal end to a second position proximate the distal end, at least a portion of the force application device is provided in the distal end, the force application device includes a distal end surface engageable to the moveable portion, the moveable portion includes a proximal end portion and a distal end portion pivotally attached to one another, and the distal end portion of the moveable portion includes the wedge portion.

6. The method of claim 5, wherein applying the force of the force application device includes translating motion of the force application device to a pushing portion attached thereto, the pushing portion translating the motion of the pushing portion to the wedge portion via the distal end surface, the proximal end portion, and the distal end portion of the moveable portion.

7. The method of claim 5, wherein the upper portion includes an outer surface configured to engage a vertebral endplate of the upper vertebral body, and the lower surface includes an outer surface configured to engage a vertebral endplate of the lower vertebral body.

8. The method of claim 5, wherein a hook-shaped projection is positioned proximate the force application device, the hook-shaped projection being engageable with a locking portion positioned on the upper portion, to at least temporarily hold the implant in the collapsed position.

9. A method of inserting an expandable spinal implant into a disc space of a patient between an upper vertebral body and a lower vertebral body, the method comprising:

providing an expandable spinal implant, the implant having a proximal end, an opposite distal end, an upper portion, a lower portion, a moveable portion, and a force application device, the upper portion and the lower portion each including an outer surface configured to contact an endplate of one of the upper vertebral body and the lower vertebral body, the upper portion and the lower portion being moveable between a collapsed position and an expanded position with respect to one another, the moveable portion being positioned between the upper portion and the lower portion, and the force application device being configured to move the moveable portion toward or away from the distal end of the implant;

surgically preparing the disc space;

inserting the implant, with the upper portion and the lower portion in the collapsed position, into the disc space;

contacting the outer surface of the upper portion to the endplate of the upper vertebral body and contacting the outer surface of the lower portion to the endplate of the lower vertebral body;

contacting a distal end surface of the force application device to the moveable portion;

applying a force with the force application device to a wedge portion of the moveable portion via the contact of the distal end surface to the moveable portion;

moving the wedge portion toward the distal end of the implant along a lower surface formed on the lower portion;

pivoting the wedge portion along a ramp portion of the lower surface of the lower portion toward at least a portion of an upper surface formed on the upper portion;

contacting the wedge portion to the upper portion and moving the upper portion away from the lower portion; and moving the implant from the collapsed position to the expanded position.

10. The method of claim 9, wherein at least one of the upper and lower surfaces includes at least one opening defined therein.

11. The method of claim 10, further comprising placing a bone growing agent through the at least one opening defined in the at least one of the upper surface and the lower surface.

12. The method of claim 9, wherein moving the upper portion away from the lower portion increases lordosis between the upper vertebral body and the lower vertebral body.

13. The method of claim 9, wherein the upper portion and the lower portion are pivotally engaged with one another, the upper portion includes an inner surface of which the upper surface is a part, the inner surface of the upper portion extends from a position intermediate the distal end and the proximal end to a second position proximate the distal end, the lower portion includes an inner surface of which the lower surface is a part, the inner surface of the lower portion extends from a position intermediate the distal end and the proximal end to a second position proximate the distal end, at least a portion of the force application device is provided in the distal end, the force application device includes a distal end surface engageable to the moveable portion, the moveable portion includes a proximal end portion and a distal end portion pivotally attached to one another, and the distal end portion of the moveable portion includes the wedge portion.

14. The method of claim 13, wherein applying the force of the force application device includes translating motion of the force application device to a pushing portion thereof, the pushing portion including the distal end surface formed thereon.

15. The method of claim 13, wherein a hook-shaped projection is positioned proximate the force application device, the hook-shaped projection being engageable with a locking portion positioned on the upper portion, to at least temporarily hold the implant in the collapsed position.

16. A method of inserting an expandable spinal implant into a disc space of a patient between an upper vertebral body and a lower vertebral body, the method comprising:

providing an expandable spinal implant, the implant having a proximal end, an opposite distal end, an upper portion, a lower portion, a moveable portion, and a force application device, the upper portion and the lower portion being moveable between a collapsed position and an expanded position, the moveable portion including a wedge portion and being positioned between the upper portion and the lower portion, and the force application device including a distal end surface and being configured to move the wedge portion of the moveable portion toward or away from the distal end of the implant via contact of the distal end surface with the moveable portion;

surgically preparing the disc space;

inserting the implant, with the upper portion and the lower portion in the collapsed position, into the disc space;

contacting the distal end surface of the force application device to the moveable portion;

applying a force with the force application device to the wedge portion of the moveable portion via the contact of the distal end surface to the moveable portion;

moving the wedge portion toward the distal end of the implant along a lower surface of the lower portion;

pivoting the wedge portion along a ramp portion of the lower surface of the lower portion toward at least a portion of an upper surface formed on the upper portion;

contacting the wedge portion to the upper portion and moving the upper portion away from the lower portion; and moving the implant from the collapsed position to the expanded position.

17. The method of claim 16, wherein at least one of the upper and lower surfaces includes at least one opening defined therein.

18. The method of claim 16, further comprising placing a bone growing agent through the at least one opening defined in the at least one of the upper surface and the lower surface.

19. The method of claim 16, wherein the upper portion and the lower portion are pivotally engaged with one another, the upper portion includes an inner surface of which the upper surface is a part, the inner surface of the upper portion extends from a position intermediate the distal end and the proximal end to a second position proximate the distal end, the lower portion includes an inner surface of which the lower surface is a part, the inner surface of the lower portion extends from a position intermediate the distal end and the proximal end to a second position proximate the distal end, at least a portion of the force application device is provided in the distal end, the moveable portion includes a proximal end portion and a distal end portion pivotally attached to one another, and the distal end portion of the moveable portion includes the wedge portion.

20. The method of claim 16, wherein the upper portion includes an outer surface configured to engage a vertebral endplate of the upper vertebral body, and the lower surface includes an outer surface configured to engage a vertebral endplate of the lower vertebral body.

* * * * *